United States Patent
Ramirez Zapata et al.

(10) Patent No.: US 10,201,164 B2
(45) Date of Patent: Feb. 12, 2019

(54) METHOD FOR INCREASING THE PRODUCTION OF FLOWERS, SEEDS AND/OR FRUIT OF A PLANT

(71) Applicants: UNIVERSIDAD POLITECNICA DE MADRID, Madrid (ES); PLANT RESPONSE BIOTECH SL, Madrid (ES)

(72) Inventors: Diana Ramirez Zapata, Madrid (ES); Maria Soledad Sacristan Benayas, Madrid (ES); Evelin Elizeth Cueva Gonzalez, Madrid (ES); Angela Alonso Gonzalez, Madrid (ES); Marise Borja Y Tome, Madrid (ES); Diego Anton Rodriguez, Madrid (ES); Rosa Maria Perez Jimenez, Madrid (ES)

(73) Assignees: UNIVERSIDAD POLITECNICA DE MADRID, Madrid (ES); PLANTRESPONSE BIOTECH SL, Madrid (ES)

( * ) Notice: Subject to any disclaimer, the term of this patent is extended or adjusted under 35 U.S.C. 154(b) by 10 days.

(21) Appl. No.: 15/104,138

(22) PCT Filed: Dec. 17, 2014

(86) PCT No.: PCT/ES2014/070930
§ 371 (c)(1),
(2) Date: Jun. 13, 2016

(87) PCT Pub. No.: WO2015/092104
PCT Pub. Date: Jun. 25, 2015

(65) Prior Publication Data
US 2016/0309724 A1    Oct. 27, 2016

(30) Foreign Application Priority Data
Dec. 17, 2013   (ES) .................... 201331839

(51) Int. Cl.
*A01N 63/04*  (2006.01)
*C12R 1/645*  (2006.01)
*A01H 3/00*   (2006.01)
*C12Q 1/6895* (2018.01)

(52) U.S. Cl.
CPC ........... *A01N 63/04* (2013.01); *A01H 3/00* (2013.01); *C12Q 1/6895* (2013.01); *C12R 1/645* (2013.01)

(58) Field of Classification Search
None
See application file for complete search history.

(56) References Cited

U.S. PATENT DOCUMENTS

2015/0119246 A1* 4/2015 Jelesko .................. A01N 63/04
                                                    504/117

FOREIGN PATENT DOCUMENTS

EP    0653162 A1 *  5/1995  ............ A01N 63/04
ES    2439393 A1    1/2014

OTHER PUBLICATIONS

P.F. Cannon et al., "Colletotrichum—current status and future directions," published online Sep. 15, 2012, Studies in Mycology 73: 181-213.*
R. O'Connell, "Good connections: fungi helping out plants," published Mar. 18, 2016, <http://presse.inra.fr/en/Press-releases/endophyte-fungi>, p. 1-2.*
USDA , "What is Soil?" Natural Resources Conservation Service Soils, <https://www.nrcs.usda.gov/wps/portal/nrcs/detail/soils/edu/?cid=nrcs142p2_054280>, p. 1.*
J. Lamp'l, "Bacteria, Fungus, and Viruses, an Overview," <https://www.growingagreenerworld.com/bacteria-fungus-and-viruses-an-overview/>, Copyright 2017, p. 1-12.*
U. Damm, et al; Colletotrichum species with curved conidia from herbaceous hosts; Fungal Diversity; Jan. 2009; XP055114671; pp. 1-43.
R.S. Redman, et al; Conversion of the pathogenic fungus colletotrichum magna to a nonpathogenic, endophytic . . . ; Molecular Plant-Microbe Interactions; APS Press; vol. 12; No. 11; Nov. 1999; XP009034000; pp. 1-7.
R. Rodriguez, et al; More than 400 million years of evolution and some plants still can't make it on their own . . . ; Journal of Experimental Botany; vol. 59; No. 5; Feb. 2008; XP055114681; pp. 1-6.
G. Tao, et al; Endophytic colletotrichum species from bletilla ochracea (*Orchidaceae*), with descriptions of . . . ; Fungal Diversity; vol. 61; No. 1; Jul. 2013; XP055114742; pp. 1-26.
International Search Report and Written Opinion dated Apr. 30, 2015 for PCT/ES2014/070930.

* cited by examiner

*Primary Examiner* — Monica A Shin
(74) *Attorney, Agent, or Firm* — Myers Bigel, P.A.

(57) ABSTRACT

The invention relates to a method for increasing the production of flowers, seeds and/or fruit of a plant, comprising the step of bringing said plant into contact with a composition comprising the micro-organism *Colletotrichum tofieldiae* and/or extracts of said micro-organism and/or filtrates of said micro-organism. Said micro-organism can be a strain of *Colletotrichum tofieldiae* deposited with the deposit number CECT 20833, CECT 20834, CECT 20835 or CECT 20836.

24 Claims, 1 Drawing Sheet
Specification includes a Sequence Listing.

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
agtctttcct gatcccgacc                                                  20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
aagtggccag atcaagtcaa                                                  20
```

METHOD FOR INCREASING THE PRODUCTION OF FLOWERS, SEEDS AND/OR FRUIT OF A PLANT

CROSS-REFERENCE TO RELATED APPLICATION

This Application is a 371 of PCT/ES2014/070930 filed on Dec. 17, 2014, which claims priority of Spanish Patent Application No. P201331839 filed Dec. 17, 2013, each of which are incorporated herein by reference.

FIELD OF THE INVENTION

The present invention may be included in the agronomic field, particularly in that of methods for increasing the production of flowers, seeds and/or fruits using the microorganism *Colletotrichum* tofieldiae.

BACKGROUND OF THE INVENTION

Plants in nature establish symbiotic associations with microorganisms referred to as mutualists conferring benefits on the growth, survival and multiplication thereof. These microorganisms can be isolated, and their beneficial properties can be used in crops so as to improve yield thereof.

The genus *Colletotrichum* (Ascomyceto, teleomorpho *Glomerella*) comprises more than 60 species and species complexes. It is morphologically characterized by typically acervular conidiomata, with or without setae, having unicellular hyaline conidia which can be straight or curved, with a size preferably bigger than 12µ, usually granular. Conidia can also be formed from mycelium or other conidia (microcyclic conidia). Conidia forms appressoria when they germinate. Some species form stromas or sclerotia.

The genus *Colletotrichum* comprises species which are important crop pathogens and which are, because of that, the most common and best studied species. However, within the genus there are many species which have been reported as being endophytes or epiphytes which cause no damage to the host plant (referred to as commensal), or which can even be beneficial for the plant (mutualists). Hyde et al. (Fungal Diversity 39 (2009) 147-182) provides a thorough description of all the species from the genus *Colletotrichum* which are currently known, including a list of hosts cited in the literature and specifying the type of interactions established with each host (pathogenic, commensal or mutualist). The evidence cited in this publication indicates that, among the species or species complexes considered as pathogenic, there may be asymptomatic strains. There are even cases of strains which behave as pathogens, commensals or mutualists depending on the host in which they are inoculated. An example of this case is *C. orbiculare*, which behaves as a pathogen in curcubitaceae but may behave as a mutualist in tomatoes, conferring resistance to pathogens and to drought and promoting the vegetative growth of the plant when it is root inoculated.

DESCRIPTION OF THE INVENTION

A preferred embodiment of the present invention is a method for increasing the production of flowers, seeds and/or fruits in a plant, characterized in that it comprises the step of contacting said plant with a composition comprising the microorganism *Colletotrichum tofieldiae* and/or extracts from said microorganism and/or filtrates from said microorganism, hereinafter referred to as "method of the invention".

Hereinafter, the term "microorganism of the invention" refers to the microorganism from the species *Colletotrichum tofieldiae*.

Increasing the production of flowers, seeds and/or fruits in a plant treated with the method of the invention should be understood as an increase in the number, size and/or weight of flowers, seeds and/or fruits of said plant compared to a plant that has not been treated according to the method of the invention.

The species *Colletotrichum tofieldiae* is described in Damm et al. ((Fungal Diversity 39 (2009) 45-87). This species is characterized by curved conidia and acervulus with setae which can be brown or black coloured. Conidia and setae can be formed directly over hyphae. Spores germinate forming appressoria featuring varied morphology and colouring. The definition of the species is also due to molecular characteristics with respect to sequences from the ribosome 5.8S subunit having the two flanking spacer regions (ITS), a 200-bp intron from the Glyceraldehyde 3-phosphate dehydrogenase (GAPDH) gene, a partial sequence from the actin (ACT) gene, chitin synthase 1 (CHS-1) gene, beta-tubulin (Tub2) gene and histone 3 (HIS3) gene. The typical isolates used to describe the species *C. tofieldiae* come from the *Tofieldia* spp. (monocotyledons), *Lupinus polyphyllus* and *Dianthus* sp. (both dicotyledoneae), therefore this species can colonize different species of hosts both from mono and dicotyledoneae. *C. tofieldiae* has not been reported as either pathogenic or mutualist for any host.

In the present invention new isolates of *Colletotrichum tofieldiae* have been isolated, identified and characterized, which surprisingly have the ability to significantly increase the production of flowers, seeds and/or fruits in plants. Isolates from other fungi species of the same area did not show this ability. Plants increase the production of flowers, seeds and/or fruits as a consequence of contacting any part of the plant with the microorganism *Colletotrichum tofieldiae* so as to establish a long lasting relationship inferring the identified increase in the production. In the present invention, the microorganism *C. tofieldiae* is shown to translocate or disperse into different organs in the treated plant, and can remain there for at least four months after treatment. This characteristic makes the microorganism effect on the plant a much longer effect, extending during the plant cycle and improving the final yield thereof. This characteristic makes this microorganism more effective than other microorganisms used for similar purposes.

The method of invention enhances the production of flowers, fruits and seeds at a ratio being higher than the increase of the vegetative growth of the plant. That is, the plant uses the resources thereof in a more efficient manner, producing more and/or bigger flowers, fruits and seeds with respect to the whole size of the plant. It is the first time this feature is described in the *Colletotrichum tofieldiae* strains of the invention. It is a phenomenon being general to the species *Colletotrichum tofieldiae*, as similar effects have been obtained with different strains of this species.

The method of the invention causes an increase in size and/or weight and/or number of flowers and/or fruits and/or seeds which can also be due to better health or viability of the crop (for example, due to reduction in the application of irrigation, fertilisers and/or pesticides, increase of systemic resistance or increase of herbicide resistance), and/or to an increase of seeds germination and/or bio-control characteristics such as a decrease in diseases associated to reduced sensitivity to pathogens and/or to amelioration of previous infections.

The method of the invention produces at least one of the following effects:
  Global increase in the plant yield;
  Increase in the quality of the plant material;
  increase in the number and/or size of flowers;
  increase in the number, size and/or weight of fruits
  increase in the number, size and/or weight of seeds.

An increase in the global yield preferably indicates an increase in the yield of the harvestable parts of the plant. The yield increase may be, for example, any type of increase such as one wherein there have been an increased number of harvestable vegetative parts and/or an increase in the weight thereof and/or an increase in the content of storage substances, metabolites of interest, etc. An increased yield of the plants means that the harvestable parts of the plant are at least 2%, preferably at least 25%, more preferably 70% and particularly preferably at least 500% higher when the plant is contacted with the composition comprising spores, mycelium and/or any other part of the microorganism of the invention, the culture medium or the filtrate according to the invention, as compared to the untreated plants.

An increase in quality preferably denotes an improvement in the desirable qualities of the plant. This increased quality may differ from one plant to the other. With regards to ornamental plants, such as for example, Petunia, an increased quality may refer to an increase in the number of flowers or leaves. With regards to cereals, an increased quality may refer to an increase in the amount of proteins or starch content in the seeds, or an desired alteration in the structure or composition of storage substances.

In the method of the invention, a plant is contacted with a composition comprising the microorganism *Colletotrichum tofieldiae*, the culture medium or the filtrate according to the invention. The composition can be applied to the entire plant or to any of the parts thereof, such as to the leaves, sprouts, flowers, fruits, cobs, seeds, bulbs, tubers, roots and to the seedlings. Application of the composition to the plant can be carried out at any stage, for example, it can be applied to the seed before the sowing, during the sowing, after the sowing, and before or after the shoot emergence, during the growing season, such as during seedbed cultivation, or at the time the seedlings are transplanted, or when plant cuttings or rooting of the cuttings take place, or at the growing period in a plantation, or even at the reproductive stage before flowering or during flowering or during the ripening process of the fruit.

Therefore, another embodiment refers to the method of the invention wherein said composition is applied to the seeds of said plant.

Another embodiment refers to the method of the invention wherein said composition is applied to aerial parts of said plant.

Another embodiment refers to the method of the invention wherein said composition is applied to the roots of said plant or to other underground parts of said plant.

The method of the invention includes spray or atomization treatment over the entire plant or any part thereof, with an appropriate dilution of the composition according to the invention, or immersion of the entire plant or of any part thereof in said dilution. The method of the invention also includes dry dusting treatment of the entire plant or of any part thereof with the composition according to the invention. The method of the invention includes seed pelleting or coating using a thin layer of a composition according to the invention. The composition according to the invention can also be mixed with the irrigation liquid. The method of the invention also includes treatment by means of agar fragments with mycelium which is contacted with one part of the plant, such as the root, stem or leaves, or even onto the soil surface near the roots of the crops.

In the present description, the term "filtrate" means a liquid culture medium obtained from growing the microorganism of the invention. It is possible to obtain a liquid culture medium being free or essentially free from the microorganism of the invention. The culture medium may be firstly prepared by growing the microorganism of the invention in a liquid culture medium, and then separating the liquid culture medium from the microorganism of the invention. Separation may be carried out by means of different methods well known to those skilled in the art, for example, by centrifugation or filtration. It is possible, for example, to heat the medium with the microorganism of the invention twice, up to about 80° C. for 30 min and then remove the fungal material by centrifugation.

Preferably, the filtrate is obtained by filtration of the culture medium through a filter having a pore size of no more than 2 μm, preferably through a filter having a pore size of no more than 0.2 μm. The filtration step allows removal of essentially all hyphae from the microorganism of the invention, more preferably the filtration should also remove spores, and even more preferably it should remove any type of fungal material.

The present invention also refers to plants that, according to the method of the invention, have been contacted with a composition comprising the microorganism *Colletotrichum tofieldiae* and/or extracts from said microorganism and/or filtrates from said microorganism, and to products produced from the harvested parts of said plants.

Another embodiment refers to the method of the invention wherein said microorganism is a strain of *Colletotrichum tofieldiae* deposited under the deposit number CECT 20833, CECT 20834, CECT 20835 or CECT 20836.

Three strains of *Colletotrichum tofieldiae* were deposited on May 30, 2013 under the provisions of the Budapest Treaty in the International Depositary Authority "Colección Española de Cultivos Tipo" (CECT, for its Spanish acronym) at the address Pare Cientific Universitat de Valencia, Catedrático Agustín Escardino, 9. 46980, Paterna, (Valencia), Spain, ad have been assigned deposit numbers CECT 20833, CECT 20834 and CECT 20835. One strain of *Colletotrichum tofieldiae* was deposited on May 7, 2013 under the provisions of the Budapest Treaty in the International Depositary Authority "Colección Española de Cultivos Tipo" (CECT) at the address Parc Cientific Universitat de Valencia, Catedrático Agustín Escardino, 9. 46980, Paterna, (Valencia), Spain, and has been assigned deposit number CECT 20836.

The deposits will irrevocably and without restriction or condition be available to the public upon issuance of a patent. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. 112. However, it should be understood that the availability of a deposit does not constitute a license to practice the subject invention in derogation of patent rights granted by government action. The deposit will be maintained without restriction in the CECT depository, which is a public depository, for a period of 30 years, or 5 years after the most recent request, or for the enforceable life of the patent, whichever is longer, and will be replaced if it ever becomes nonviable during that period.

The microorganism of the invention can be grown over a wide variety of natural or synthetic substrates. For example, it can be grown in different solid or liquid culture media, such as Potato/Dextrose/Agar (PDA) medium or broth (PDB), and it can be propagated by means of techniques being known per se by those skilled in the art. It can also grow over several natural sources, such as leaves from several plants, pollen grains, oat flower, potato, carrot and cellulose. It can also grow over artificial sources such as paper or cardboard and polymers.

The culture medium can be under constant stirring during the culture, for example at approximately 1 rps. Furthermore, the culture temperature can be within a range from 20 to 30° C.

Another embodiment refers to the method of the invention, wherein said microorganism is in the form of spores, hyphae, mycelium or sclerotia.

Another embodiment refers to the method of the invention wherein said composition is applied to the substrate for the cultivation of said plant.

The substrate is preferably treated such that the microorganism of the invention is grown therein before said substrate is used for the plants cultivation. Examples of substrate treatment include infusing a liquid into the substrate (by means of irrigation, injection or dripping), spraying, dusting or direct mixing with the substrate. The method of the invention also comprises treating a hydroponic medium, for hydroponic cultivation. The method of the invention consists of treating the substrate or hydroponic medium with a composition comprising the suitable concentration of mycelium and/or spores and/or any other part of the microorganism of the invention, the culture medium or filtrate according to the invention in liquid form and/or in solid form as granules or dust.

The method of the invention can be carried out with a composition including the microorganism of the invention either alone or formulated with inert ingredients. Examples of inert ingredients include fine powder or granules such as minerals, clays, bentonite, calcite, diatoms and organic materials such as corn powder or nut shell powder, synthetic organic materials such as urea, salts such as calcium carbonate and ammonium sulphate, synthetic inorganic materials such as silicon oxide; or liquid diluents such as aromatic hydrocarbons as xylene, alkyl benzene, methyl naphthalene, alcohols such as 2,5-propanol, ethylene glycol, glycol propylene, and ethylene glycol monoethyl ether, ketones such as acetone, cyclohexanone and isophorone, vegetable oils such as soya oil or cotton-seed oil, aliphatic hydrocarbons derived from petroleum, esters, dimethyl sulfoxide, acetonitrile and water. Examples of surfactants include anionic surfactants such as alkyl sulphate ester salts, alkyl aryl sulfonate salts, dialkylsulfosuccinate salts, polyoxyethylene alkyl aryl ether phosphate ester salts, lignosulphonate salts and formaldehyde polycondensates, and non-ionic surfactants such as polyoxyethylene alkyl aryl ethers, alkyl polyoxypropylene block copolymers, polyoxyethylene and fatty acid esters, and cationic surfactants such as alkyltrimethylammonium salts. Examples of other auxiliary formulation agents include water soluble polymers such as polyvinyl alcohol or polyvinylpyrrolidone, polysaccharides such as agar, acacia gum, alginic acid and salts thereof, carboxymethyl cellulose, xanthan gum, inorganic materials such as aluminium and magnesium silicate, preservatives, colouring agents, stabilising agents such as isopropyl acid phosphate and BHT.

Therefore, another embodiment refers to the method of the invention wherein said composition comprises minerals, organic materials, organic compounds, inorganic compounds, liquid diluents, alcohols, ketones, vegetable oils, aliphatic hydrocarbons, esters, dimethyl sulfoxide, acetonitrile, water, anionic surfactants, non-ionic surfactants, cationic surfactants, water soluble polymers, polysaccharides, preservatives, colouring agents, and/or stabilising agents. Particularly, said minerals are selected from the group consisting of clays, bentonite, calcite and diatoms, said organic materials are selected from the group consisting of corn powder or nut shell powder, said organic compound is urea, said inorganic compounds are selected from the group consisting of calcium carbonate, ammonium sulphate, silicon oxide, aluminium and magnesium silicate, said liquid diluents are selected from the group consisting of aromatic hydrocarbons, aliphatic hydrocarbons, alcohols, ketones, vegetable oils, esters, dimethyl sulfoxide, acetonitrile and water, said anionic surfactants are selected from the group consisting of alkyl sulphate ester salts, alkyl aryl sulfonate salts, dialkylsulfosuccinate salts, polyoxyethylene alkyl aryl ether phosphate ester salts, lignosulphonate salts and formaldehyde polycondensates, said non-ionic surfactants are selected from the group consisting of polyoxyethylene alkyl aryl ethers, alkyl polyoxypropylene block copolymers, polyoxyethylene and fatty acid esters, said cationic surfactants are alkyltrimethylammonium salts, said water soluble polymers are polyvinyl alcohol or polyvinylpyrrolidone, said polysaccharides are selected from the group consisting of agar, acacia gum, alginic acid, alginic acid salts, carboxymethyl cellulose and xanthan gum, and said stabilising agents are isopropyl acid phosphate and BHT. Particularly, said aromatic hydrocarbons are selected from the group consisting of xylene, alkyl benzene, methyl naphthalene, said alcohols are selected from the group consisting of 2,5-propanol, ethylene glycol, glycol propylene, and ethylene glycol monoethyl ether, said ketones are selected from the group consisting of acetone, cyclohexanone and isophorone, and said vegetable oils are soya oil or cotton-seed oil.

Another embodiment refers to the method of the invention wherein said composition comprises organic irrigation salts, fertilizers, insecticides, nematicides, fungicides, bactericides and/or herbicides.

Another embodiment refers to the method of the invention wherein said composition is a liquid, a solid, a paste or a gel.

Another embodiment refers to the method of the invention wherein said composition is in the form of powder, pastille, tablet, granule or emulsifiable concentrate.

Another embodiment refers to the method of the invention wherein said composition is applied by spraying, atomization, immersion, irrigation or dusting.

Another embodiment refers to the method of the invention wherein said plant is selected from the group consisting of gymnospermae, monocotyledons and dicotyledoneae. Particularly, said plant is a plant from the Brassicaceae family.

Another embodiment refers to the method of the invention wherein said plant is a monocotyledon plant.

Another embodiment refers to the method of the invention wherein said plant is a barley plant (*Hordeum vulgare*).

Another embodiment refers to the method of the invention wherein said plant is a corn plant (*Zea mays*).

In the present invention, the plant can be a natural or transgenic plant.

The method of the invention can be carried out with all possible plants and cells or tissues derived from said plants. In particular, they can be carried out with all gymnospermae and angiospermae (monocotyledons or dicotyledoneae) or plant material derived from said plants, including trees, shrub, grasses and lawn. Preferably, the uses and processes are applied to be used in useful plants or materials or such plants cells, more preferably for agriculture, horticulture, forest plants, ornamental plants, or of any other commercial interest. Among others, being illustrative and non-limitative of the scope of the present invention, these may be: rice, wheat, barley, corn, soya, rape, tomato, bean, as well as different fruit (orange tree, lemon tree, etc.) and ornamental species.

Another embodiment of the invention refers to a plant propagation material comprising the microorganism *Colletotrichum tofieldiae* and/or extracts form said microorganism and/or filtrates from said microorganism. Particularly, said propagation material is selected from the group consisting of seeds, seedlings, young plants, cuttings, bulbs or tubers.

"Propagation material" means herein any type of cell material from which a plant can germinate or develop. Examples of propagation material include, but are not limited to: seeds, cuttings, cell suspensions, callus culture, tissue culture, protocorms, explants or germplasm. The propagation material may have a different origin. For example, it can be freshly collected, or be derived from a stock, such as a seed sample or a frozen cells stock.

Another embodiment of the invention refers to a substrate for the cultivation of plants comprising the microorganism *Colletotrichum tofieldiae* and/or extracts from said microorganism and/or filtrates from said microorganism.

The substrate for the cultivation of plants may comprise the spore, mycelium or any other part of the microorganism of the invention or the culture medium or filtrate thereof, or any of the possible combinations of some of these components. The substrate may be liquid or solid.

Examples of substrates for the cultivation of plants are natural or synthetic media being solidified, and those intended for plant cultivation especially in vitro. Other examples are soil, sand, humus or peat or a mixture thereof.

Another embodiment of the invention refers to a strain of the microorganism *Colletotrichum tofieldiae*, deposited under the deposit number CECT 20833, CECT 20834, CECT 20835 and CECT 20836.

Another embodiment of the invention refers to the use of the microorganism *Colletotrichum tofieldiae* and/or extracts from said microorganism and/or filtrates from said microorganism for increasing the production of flowers, seeds and/or fruits in a plant.

Another embodiment of the invention is the use of the microorganism *Colletotrichum tofieldiae* and/or extracts from said microorganism and/or filter media from said microorganism so as to increase the production of chlorophyll in a plant.

Another embodiment of the invention refers to the use of the microorganism *Colletotrichum tofieldiae* and/or extracts from said microorganism and/or filter media from said microorganism for increasing the production of flowers, seeds and/or fruits in a plant undergoing drought or limited irrigation conditions.

Another embodiment of the invention refers to the primers identified by sequences SEQ ID NO: 1 and 2.

PREFERRED EMBODIMENTS

Example 1: Screening of Fungi which Increase Plant Productivity

*Arabidopsis thaliana* plants growing under natural conditions were recollected. These plants lacked of symptoms of disease such as chlorosis, leaf stains and other type of lesions induced by pathogens. Fragments of the rosette leaves from the collected plants were disinfected by submerging them in 20% commercial bleach (1% active chlorine) and by softly stirring for 5 minutes. Then, the fragments were rinsed twice in sterile water and placed in a humidity chamber at room temperature (20-24° C.).

The fragments were periodically inspected, isolated the mycelium emerging onto Petri dishes with potato dextrose agar (PDA) medium having 200 mg/L of chloramphenicol. From all the isolates obtained, a screening was made so as to find fungi which were beneficial in producing an increase in the production of seeds in a plant (Table 1). In order to realize the screening tests, superficially sterilized *Arabidopsis thaliana* seeds, accession Col-0, were sown into sterile substrate (peat and vermiculite at 3:1 ratio). They were stratified at 4° C. for 3 days and then kept in a controlled growth chamber at 23° C. Plants were treated when they were 3 weeks old (having 4-6 leaves) by applying a portion of 3 mm of diameter of the mycelium from any of the isolates onto a leaf. The mycelium had been obtained by sub-culture of the fungus mycelium derived from a wild type *Arabidopsis thaliana* plant with no symptoms of disease, onto PDA plates.

The control plants were not applied any treatment and were arranged randomly among the treated plants. Upon dehiscence of the scapes, these were covered with paper bags to collect the seeds. When the plants were dried, the seeds were collected and weighted. The rest of the aerial part of the plant was also weighted. From among all the isolates analysed, the isolate CECT 20833 belonging to the genus *Colletotrichum* was selected, since the plants treated with this isolate significantly increased (P<0.04) their production of seeds, being the weight of the seeds from the treated plants higher than that of the untreated plants (Table 1). The weight of the rest of the plant was not significantly different (P>0.05, Table 1).

TABLE 1

Weights (mean ± standard error) of the seeds and dry weight of the rest of the plant in mycelium treated or untreated plants according to the description in Example 1.

| | Control Plants | | Treated Plants | |
|---|---|---|---|---|
| TREATMENT | Weight of seeds Per plants (mg) | Dry weight rest of the plant (mg) | Weight of seeds Per plants (mg) | Dry weight rest of the plant (mg) |
| *Alternaria* sp. | 28.0 ± 2.9$^a$ | 177.9 ± 12.1$^a$ | 21.6 ± 2.2$^b$ | 151.1 ± 5.8$^b$ |
| ***Colletotrichum* sp. CECT 20833 | 2.8 ± 1.1$^a$ | 85.1 ± 7.7 | 8.8 ± 1.7$^b$ | 90.7 ± 4.1** |
| *Plectosphaerella* sp. | 30.3 ± 5.8 | 218.9 ± 17.2 | 27.8 ± 4.1 | 233.6 ± 112.1 |
| *Trichoderma* sp. | 14.9 ± 1.6 | 143.8 ± 10.1$^a$ | 16.5 ± 1.5 | 184.8 ± 11.6$^b$ |
| *Trichoderma* sp. | 15.2 ± 1.8 | 101.5 ± 11.7 | 16.2 ± 1.6 | 126.3 ± 10.2 |
| *Ulocladium* sp. | 20.3 ± 3.1 | 169.7 ± 10.4 | 19.6 ± 1.8 | 166.0 ± 7.2 |

Different letters indicate significant differences between treated plants and control plants (P < 0.05) according to an ANOVA test. The plants treated with the isolate CECT 20833 of the genus *Colletotrichum* (in bold) had a seed weight significantly higher than control plants, while the dry weight of the rest of the plant was not significantly higher.

Example 2: Identification of Isolates from the *Colletotrichum* sp. of Wild Type *Arabidopsis thaliana* Plants Such as *Colletotrichum tofieldiae*

The isolate CECT 20833 from the genus *Colletotrichum* from the screening in Example 1 showed a dark mycelium and curved hyaline conidia in acervulus having dark setae. Other isolates obtained in the same way, identified as CECT 20834, CECT 20835, and CECT 20836, showed a similar morphology. All these isolates were identified as *Colletotrichum tofieldiae* according to the morphology and sequences of several loci described in Damn et al. (Fungal Diversity 39 (2009) 45-87) which were compared to isolates sequences models deposited in the data base which can be accessed at http://www.cbs.knaw.nl/*Colletotrichum*/, hosted at the Central Bureau of Fungi Cultures (CBS, Centraalbureau voor Schimmelcultures).

The morphology of these isolates coincide with that described at Damn et al. (Fungal Diversity 39 (2009) 45-87) for *C. tofieldiae*, adding that the culture in PDA medium (agar dextrose potato) or equivalent, or in filter paper or in leaves from *A. thaliana* produces very dark colonies, that the mycelium in culture darkens and hardens with time and that it may feature thickening structures of the chlamydospores and/or microsclerotia type.

Sequence similarity (No. of identical nucleotides/No. of overlapping nucleotides) of the sequences compared between the isolates CECT 20833, CECT 20834, CECT 20835 and CECT 20836, and the model isolates CBS 168.49, CBS 495.85 and IMI 288810 from the Central Bureau of Fungi Cultures, used in Damn et al. (Fungal Diversity 39 (2009) 45-87) to define the species *C. tofieldiae*, was higher than 92%. The compared sequences were those of ribosome 5.8S subunit having the two flanking spacer regions (ITS, similarity >95%), a 200-bp intron from the Glyceraldehyde 3-phosphate dehydrogenase gene (GAPDH, similarity >92%), a partial sequence from the actin gene (ACT, similarity >99%), and histone 3 gene (HIS3, similarity >98%). These comparisons have been made using the MycoID tool for sequence pair alignment hosted at the MycoBank webpage (www.mycobank.org) from the International Mycological Association.

These characteristics together define the one or different species of *Colletotrichum* corresponding to the microorganism of the present invention.

Example 3: Isolates of *Colletotrichum tofieldiae* Persisted in Treated Plants at Least Two Months after Inoculation and were Translocated or Dispersed into Other Organs Different to the Inoculated Leaf, Such as the Root, Crown, Other Leaves or Stems Superficially sterilized *Arabidopsis thaliana* seeds, accession Col-0, were sown into sterile substrate (peat and vermiculite at 3:1 ratio). They were stratified at 4° C. for 3 days and then kept in a controlled growth chamber at 23° C., in short cycles (10 hours of light daily). Plants were treated when they were 3 weeks old with the isolates CECT 20833, CECT 20834 and CECT 20835 from *Colletotrichum tofieldiae* by the application on three leaves of a drop of a spores suspension at $10^6$ spores/ml. The entire plants were recollected 60 days post inoculation (dpi).

Figure 1:
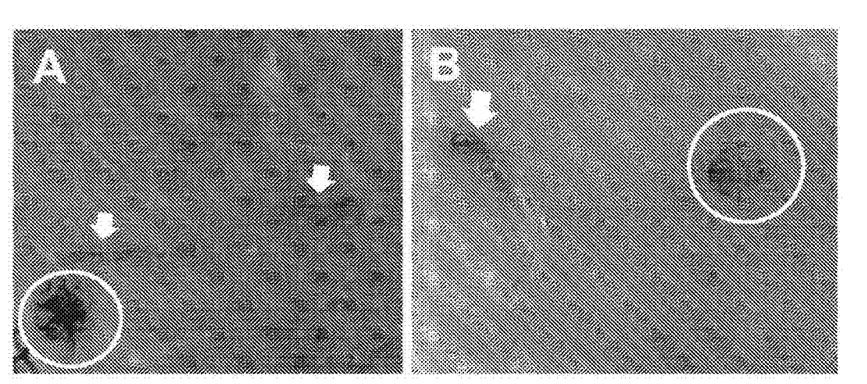
FIG. 1. Re-isolation of *C. tofieldiae* non-inoculated organs of *A. thaliana* plants 60 days after inoculation. A. re-isolated CECT 20834 isolate from the leaf (circle) and stems (arrows). B. re-isolated CECT 20834 isolate from the root (arrow) and the root crown (circle).

Roots, rosette leaves and stems were separated and cut in fragments of about 25 mm$^2$, they were disinfected as described above and incubated in a humidity chamber at room temperature. After a week, *Colletotrichum tofieldiae* was re-isolated from at least a sample of all the inoculated plants. The fungus was re-isolated from leaves different to those inoculated, from the crown, the roots and the stem (Table 2, FIG. 1). No growth of *C. tofieldiae* was observed in any of the control plants treated with distilled water.

TABLE 2

Percentage of plants from which *C. tofieldiae* was re-isolated from organs different to those inoculated (leaves, stems, crown or rootI) 60 days after treatment.

| | Re-isolation percentage | | | | |
|---|---|---|---|---|---|
| Isolate | Leaves | Stem | Crown | Root | Total[1] |
| CECT 20833 | 80% | 0% | 67% | 33% | 100% |
| CECT 20834 | 100% | 17% | 50% | 83% | 100% |
| CECT 20835 | 100% | 8% | 75% | 67% | 100% |

[1]Percentage of plants from which *C. tofieldiae* was re-isolated in at least a sample of a non-inoculated organ.

Example 4: The Isolate CECT 20834 from *Colletotrichum tofieldiae* Increased the Production of Seeds and Seed Weight Per Plant in Plants Treated with Mycelium or Spores Superficially sterilized *Arabidopsis thaliana* seeds, accession Col-0, were sown into sterile substrate (peat and vermiculite at 3:1 ratio); they were stratified at 4° C. for 3 days and then kept in a controlled growth chamber at 23° C. When they were 3 weeks old, they underwent any of the following treatments: a) Treatment with a mycelium portion from isolate CECT 20834 as in example 1; b) Application of a spore suspension from isolate CECT 20834 in sterile distilled water at a concentration of $10^6$ spores/ml sprayed over the entire plant and substrate underneath; c) Control treatment consisting of the application of sterile distilled water sprayed over the entire plant and the substrate underneath.

In the case of treatment b, the spores were obtained by resuspending in sterile distilled water the spores obtained from the fungi culture in PDA medium. The plants undergoing each of the treatments were randomly arranged. Upon dehiscence of the scapes, these were covered with paper bags to collect the seeds. When the plants were dried, the seeds were collected and weighted. The rest of the aerial part of the plant was also weighted.

The seed production per plant was measured as the weight of all the seeds harvested from each plant at the end of the cycle. The production of seeds by the plants treated with CECT 20834 was significantly higher than that of the control plants ($P<0.001$), with a weight increase of 37% for the plants treated with mycelium and 56% for plants treated with the sprayed spore suspension (Table 2). The increase in the seeds production is partly due to the production of heavier seeds, since the weight of 100 seeds from the plants treated with CECT 20834 showed a significant increment ($P<0.06$) of up to 42% with respect to the control plants. The dry weight of the rest of the plant was not significantly different ($P>0.10$). The fungus was re-isolated, 6 weeks after treatment, from 75% of the plants inoculated with mycelium and 100% of the plants inoculated by spraying. This example shows that the capacity to increase the production of seeds is not exclusive of isolate CECT 20833, but it can be extended to other isolates of *C. tofieldiae*, and that treatment with spores provides similar results to treatment with mycelium.

Example 5: The Isolates CECT 20835 and CECT 20836 from *Colletotrichum tofieldiae* Increase the Production of Seeds (Weight of the Seed Per Plant) in Plants Treated with a Spore Suspension Applied by Spraying. The Increase is Proportional to the Fungus Persistence in the Plant Superficially sterilized *Arabidopsis thaliana* seeds, accession Col-0, were sown into sterile substrate (peat and vermiculite at 3:1 ratio), stratified at 4° C. for 3 days and then kept in a controlled growth chamber at 23° C. When they were 3 weeks old, they underwent any of the following treatments: a) Application of a spore suspension from isolate CECT 20835 from *Colletotrichum tofieldiae* sp; b) Application of a spore suspension from isolate CECT 20836 from *Colletotrichum tofieldiae* sp; c) Control treatment consisting of the application of sterile distilled water. All treatments were sprayed over the entire plant and the soil underneath.

Inoculum of treatments a, b and c comes from spore suspensions kept in 30% glycerol at −80° C. and diluted in sterile distilled water at a concentration of $10^6$ spores/ml. After applying the treatment, the plants were kept at 25° C., short cycle. Two weeks after treatment, the fungus was re-isolated from 17% of the plants inoculated with CECT 20835, 20% of the plants inoculated with CECT 20836 and from none of the plants treated only with water. Six weeks after treatment, the fungus was re-isolated from 60% of the plants treated with CECT 20835 and from none of the plants treated with CECT 20836 or only with water. Upon dehiscence of the scapes, these were covered with paper bags to collect the seeds. When the plants were dried, the seeds were collected and weighted. The rest of the aerial part of the plant was also weighted.

The seed production per plant was measured as the weight of all the seeds harvested from each plant at the end of the cycle. The ANOVA of the seeds weights indicates significant differences in the average weight of seeds per plant, between plants undergoing the different treatments ($P<0.0001$, Table 4): Plants treated with CECT 20835 showed the higher average weight of seeds per plant, with an increase of 550% with respect to the plants only treated with water, and the plants treated with CECT 20836 featured an increase in the average weight of seeds of 400% with respect to the plants only treated with water. No significant differences were observed in the weight of the plants with no seeds ($P>0.10$).

TABLE 3

Weights (mean ± standard error) of the seeds per plant and 100 seeds per each plant, and dry weight of the rest of the plant (plant without seeds), of the plants treated with mycelium or spore suspension from isolate CECT 20834 or distilled water spraying, according to the description of Example 4.

| TREATMENT | Weight of seeds Per plants (mg)* | Weight of 100 seeds per plant (mg)* | Dry weight of the plant without seeds (mg)* |
|---|---|---|---|
| Distilled water spraying | 35.0 ± 3.6$^a$ | 1.17 ± 0.11$^a$ | 213.9 ± 12.0 |
| Mycelium | 47.5 ± 3.7$^b$ (37%) | 1.66 ± 0.13$^b$ (42%) | 249.3 ± 15.3 (16%) |
| Spore suspension spraying | 56.1 ± 2.9$^b$ (56%) | 1.65 ± 0.19$^b$ (41%) | 239.6 ± 16.9 (12%) |

*Different letters show significant differences according to ANOVA ($P < 0.001$, for the weight of seeds per plant and $P < 0.06$ for the weight of 100 seeds). No significant differences were found in the weight of the plant with no seeds ($P > 0.10$). The percentage increase, comparing treated plants and untreated plants, is indicated between brackets.

This example shows that the effect of applying *Colletotrichum tofieldiae* can be proportional to the persistence of the fungus in the plant.

TABLE 4

Weights (mean ± standard error) of the seeds per plant and dry weight of the rest of the plant (plant without seeds), of the plants treated as described in Example 5.

| TREATMENT | Weight of seeds Per plants (mg)* | Dry weight of the plant without seeds (mg)* |
|---|---|---|
| Distilled water spraying | 5.7 ± 2.7[a] | 273.6 ± 14.9 |
| Suspension of spores from CECT 20835 | 38.7 ± 2.5[b] (550%) | 266.2 ± 20.7 |
| Suspension of spores from CECT 20836 | 30. ± 2.7[b] (400%) | 232.9 ± 15.5 |

*Different letters show significant differences according to an ANOVA between the different treatments ($P < 0.0001$). The weight of the rest of the plant was not significantly different among the different treatments ($P > 0.10$). The percentage increase, comparing plants treated with the different isolates and control plants, is indicated between brackets.

Example 6: *Colletotrichum tofieldiae* Increased the Number of Fruits in the Plants Treated with a Spore Suspension, Both in Plants Sown in Sterile Substrate and in Plants Sown in Non-Sterile Substrate Superficially sterilized *Arabidopsis thaliana* seeds, accession Col-0, were sown into sterile and non-sterile substrate (peat and vermiculite at 3:1 ratio). They were stratified at 4° C. for 3 days and then kept in a controlled growth chamber at 23° C. When they were 3 weeks old, they underwent any of the following treatments: a) Application of a spore suspension from isolate CECT 20833 from *C. tofieldiae*; b) Application of a spore suspension from isolate CECT 20835 from *C. tofieldiae*; c) Application of sterile distilled water. All treatments were sprayed over the entire plant. Inoculum of treatments a and b comes from spore suspensions kept in 30% glycerol at −80° C., washed and diluted in sterile distilled water at a concentration of $10^6$ spores/ml. The plants were randomly distributed. The number of fruits per plant was counted at the moment the opening of siliquae. The results are shown in Table 5. The plants treated with isolates CECT 20833 and CECT 20835 from *C. tofieldiae* featured a significant increase of fruits of up to 39%. This experiment shows that the increase in the production of seeds is partly due to the production of a higher amount of fruits per plant. This experiment shows that the effect of the fungus is kept in plants over non-sterile substrate.

TABLE 5

Number of fruits (mean ± standard error) per plant treated with a spore suspension from different isolates from *C. tofieldiae* as described in Example 6.

| | No. of fruits* Sterile substrate | Non-sterile substrate |
|---|---|---|
| Distilled water spraying | 53.3 ± 6.5[a] | 11.3 ± 0.7[a] |
| *C. tofieldiae* CECT 20833 | 73.9 ± 7.0[b] (39%) | 14.7 ± 1.4[b] (31%) |
| *C. tofieldiae* CECT 20835 | 60.4 ± 5.8[b] (13%) | 14.3 ± 0.8[b] (27%) |

*Different letters indicate significant differences in an ANOVA test ($P < 0.08$ for the sterile substrate and $P < 0.04$ for the non-sterile substrate). The percentage increase, comparing treated plants with untreated plants, is indicated between brackets.

Example 7: *Colletotrichum tofieldiae* Increased the Number of Fruits in the Plants Sown in Substrates (Sterile or Non-Sterile) Treated with a Spore Suspension Superficially sterilized *Arabidopsis thaliana* seeds, accession Col-0, were sown into sterile and non-sterile substrate (peat and vermiculite at 3:1 ratio). They were stratified at 4° C. for 3 days and then kept in a controlled growth chamber at 23° C. When they were 3 weeks old, 200 µl of a) a spore suspension from isolate CECT 20833 from *C. tofieldiae*; b) a spore suspension from isolate CECT 20835 from *C. tofieldiae*; c) sterile distilled water, were deposited in the substrate next to the plant. Inoculum of treatments a and b comes from spore suspensions kept in 30% glycerol at −80° C., washed and diluted in sterile distilled water at a concentration of $10^6$ spores/ml. The plants were randomly distributed. The number of fruits per plant was counted at the moment the opening of siliquae. The results are shown in Table 6. The plants treated with isolates CECT 20833 and CECT 20835 from *C. tofieldiae* feature an increase in fruits of up to 27%.

TABLE 6

Number of fruits (mean ± standard error) per plant treated with a spore suspension from different isolates from *Colletotrichum* directly applied onto the substrate as described in Example 7.

| | No. of fruits* Sterile substrate | Non-sterile substrate |
|---|---|---|
| Distilled water spraying | 53.8 ± 6.0 | 16.6 ± 1.5 |
| *C. tofieldiae* CECT 20833 | 64.8 ± 7.0 (20%) | 17.9 ± 1.5 (8%) |
| *C. tofieldiae* CECT 20835 | 68.4 ± 7.3 (27%) | 17.6 ± 5.1 (6%) |

*The percentage increase, comparing treated plants with untreated plants, is indicated between brackets.

Example 8: *Colletotrichum tofieldiae* Persisted in Treated Corn and Rape Plants, at Least 38 Days Post Inoculation Superficially sterilized corn seeds from FAO700 variety, and rape seeds from Westar variety were sown into sterile substrate (peat and vermiculite at 3:1 ratio), and then kept in a controlled growth chamber at 23° C., short cycle (10 hours of light daily). When they were 3 weeks old, plants were treated with the isolate CECT 20833 from *C. tofieldiae* by spraying 120 ml of a spore suspension at $10^6$ spores/ml in the presence of 0.75% of surfactant (alkyl polysaccharide). The first and the second leaves were recollected from seven plants 23 dpi, while the third and the fourth leaves were recollected 38 dpi.

Leaves were separated and cut into fragments of about 25 $mm^2$, they were disinfected as described above and incubated in a humidity chamber at room temperature. After a week, *C. tofieldiae* was re-isolated from at least 64.3% of the samples recollected 38 dps from seven inoculated corn plants and 7% of the samples recollected from seven inoculated rape plants (Table 7). No growth of *C. tofieldiae* was observed in any of the control plants treated with distilled water.

TABLE 7

Number of corn or rape leaves and percentage of that from which
C. tofieldiae was re-isolated 23 days (first and second leaves)
and 38 days (third and fourth leaves) after treatment.

| Culture | Days post spray | Leaf sample (seven plants) | Number of corn Leaves having Acervuli (seven Plants) | Re-isolation percentage per leaf | Re-isolation Percentage of the leaf of the Same plant |
|---|---|---|---|---|---|
| Corn | 23 | Leaf 1 | 1 | 14.3% | 42.8% |
|  |  | Leaf 2 | 5 | 71.4% |  |
|  | 38 | Leaf 3 | 5 | 71.4% | 64.3% |
|  |  | Leaf 4 | 4 | 57.1% |  |
| rape | 23 | Leaf 1 | 7 | 100% | 78.6% |
|  |  | Leaf 2 | 4 | 57.14% |  |
|  | 38 | Leaf 3 | 0 | 0% | 7% |
|  |  | Leaf 4 | 1 | 14.28% |  |

Example 9: *Colletotrichum tofieldiae* can be Inoculated by Means of Different Methods in Corn and Barley, it is Translocated from Seeds and Roots into Leaves, and Increases the Content in Chlorophylls Washed corn seeds of the FAO700 variety and barley seeds of the Arturio variety were treated by means of different treatments (36 plants per treatment):
1. Immersion treatment: seeds were inoculated by immersion for 2 h in a shaken mycelium suspension from the isolate CECT 20833, grown in PDB for 10 days, at an optical density of 1.2, and were sown in a substrate consisting of a mixture of peat and vermiculite at a 3:1 ratio.
2. Rye treatment: the seeds were sown in a substrate consisting of a mixture of peat and vermiculite at a 3:1 ratio to which rye seeds were added (35 g/l substrate) which have been inoculated 8 days before with mycelium discs from isolate CECT 20833.
3. Peat treatment: seeds were sown in a substrate consisting of a mixture of peat and vermiculite at a 3:1 ratio, to which a mixture of peat and bran (20 g/l substrate) was added, said mixture which had been inoculated two weeks before with spores from isolate CECT 20833. A quantity of $1.5 \times 10^4$ spores/gram of peat and bran mixture.
4. Spray treatment: the seeds were sown in a substrate consisting of a mixture of peat and vermiculite at a 3:1 ratio, and when they were 3 weeks old they were inoculated by spraying 120 ml of a suspension of mycelium from the isolate CECT 20833, which had grown in PDB for 10 days, set to an optical density of 1.2 in the presence of 0.75% surfactant (alkyl polysaccharide).
5. Irrigation treatment: seeds were sown in a substrate consisting of a mixture of peat and vermiculite at a 3:1 ratio, and they were inoculated by irrigation (5 ml) with a shaken mycelium suspension from isolate CECT 20833, which had been grown in PDB for 10 days, set to an optical density of 1.2.

Once sown, the plants were kept in a greenhouse at 23° C., in short cycle (10 hours of light daily). After 25 days, leaves were separated and cut into about 25 mm² fragments, they were disinfected as previously described and incubated in a humidity chamber at room temperature. After a week, *C. tofieldiae* was re-isolated from all rye treatments and all corn treatments except for seed immersion (Table 8). No growth of *C. tofieldiae* was observed in any of the control plants treated with distilled water. Furthermore, after three months, the plants were sampled and leaf tissue was taken which was kept for 18 hours in 80% ethanol. After this time, absorbance was measured from the suspension ($DO_{663}$) as an indicator for the chlorophyll a concentration. In rye and peat treatments absorbance was found to be significantly higher than in non-inoculated control plants (Table 9).

TABLE 8

Re-isolation percentage of isolate CECT 20833 from corn and barley
plants after the different treatments and absorbance of corn samples
$DO_{663}$ (chlorophyll a).

| Treatment | N | Corn: Re-isolation percentage | Rye: Re-isolation percentage | Corn: Absorbance $DO_{663}$ (chlorophyll a)* |
|---|---|---|---|---|
| Control Immersion | 32 | 0% | 0% | — |
| Immersion | 32 | 0% | 20% | — |
| Control rye | 32 | 0% | 0% | $0.24 \pm 0.02^a$ |
| rye | 32 | 90% | 40% | $0.33 \pm 0.03^b$ |
| Control Peat | 32 | 0% | 0% | $0.15 \pm 0.02^a$ |
| Added Peat | 32 | 80% | 10% | $0.25 \pm 0.02^b$ |
| Control Spray | 32 | 0% | 0% | $0.42 \pm 0.02^a$ |
| Spray | 32 | 30% | 50% | $0.37 \pm 0.02^a$ |
| Control irrigation | 32 | 0% | 0% | $0.17 \pm 0.02^a$ |
| irrigation | 32 | 70% | 50% | $0.16 \pm 0.02^a$ |

*Different letters indicate significant differences in an ANOVA ($P < 0.05$)

Example 10: *Colletotrichum tofieldiae* can be Inoculated as Conidia or Mycelium, Both in the Substrate and in Spray on Corn. It is Mobilized from the Root to the Leaves and Vice Versa, Increasing the Chlorophyll Content Washed corn seeds of the variety FAO700 underwent different treatments (54 plants per treatment):
1. Peat-mycelium treatment: seeds were sown in a peat:vermiculite substrate (3:1) plus a mixture of peat and barn (20 g/l) inoculated with a shaken mycelium suspension from the isolate CECT 20833 as described in Example 9.
2. Peat-spores treatment: seeds were sown in a peat:vermiculite substrate (3:1) plus a mixture of peat and barn (20 g/l) inoculated two weeks before with a spore suspension at $10^6$ spores/ml from isolate CECT 20833.
3. Spray-spores treatment: the seeds were sown in a peat:vermiculite substrate (3:1) and plants were inoculated when they were 3 weeks old with the isolate CECT 20833 from *C. tofieldiae* by spraying 120 ml of a spore suspension at $10^6$ spores/ml in the presence of 0.5% surfactant (alkyl polysaccharide).
4. Spray-mycelium treatment: the seeds were sown in a peat:vermiculite substrate (3:1) and plants were inoculated when they were 3 weeks old with the isolate CECT 20833 from *C. tofieldiae* by spraying 120 ml of a mycelium suspension at an optical density of 1.5 in the presence of 0.5% surfactant (alkyl polysaccharide).

Once sown, the plants were kept in a greenhouse at 23° C., in short cycle (10 hours of light daily) for 8 weeks. Leaves or roots were separated and cut into about 25 mm² fragments, they were disinfected as previously described and incubated in a humidity chamber at room temperature. After 30 days, *C. tofieldiae* was re-isolated from all treatments (Table 9). No growth of *C. tofieldiae* was observed in any of the control plants treated with distilled water spray, or sown with peat. Furthermore, the chlorophyll content index (ICC) was measured using the opti-sciences CCM 200 measuring device. In all treatments absorbance inoculated plants were found to have significantly higher ICC than non-inoculated control plants, except for spores spray treatment (Table 9).

TABLE 9

Re-isolation percentage in the roots and leaves from corn plants and chlorophyll content (ICC) (mean ± standard error) after different treatments.

| Treatment | N | Root: Re-isolation percentage | Leaf: Re-isolation percentage | N (number of Measurements) | ICC* |
|---|---|---|---|---|---|
| Control peat mycelium | 54 | 0% | 0% | 50 | 2.82 ± 0.09$^a$ |
| peat mycelium | 54 | 67% | 20% | 38 | 3.57 ± 0.12$^b$ |
| Control peat spores | 54 | 0% | 0% | 56 | 3.27 ± 0.14$^a$ |
| Peat spores | 54 | 67% | 25% | 34 | 3.78 ± 0.16$^b$ |
| Control spores mycelium | 54 | 0% | 0% | 60 | 3.97 ± 0.13$^a$ |
| Mycelium spray | 54 | 33% | 45% | 48 | 5.84 ± 0.44$^b$ |
| Spores spray control | | | 0% | 70 | 3.46 ± 0.10a |
| Spores spray | 54 | 42% | 35% | 64 | 2.99 ± 0.10$^b$ |

*Different letters indicate significant differences in an ANOVA (P < 0.05)

Example 11: *Colletotrichum tofieldiae* Increased the Number of Grains Per Cob and the Weight Per Cob in Corn Plants Treated with the Isolate CECT 20833 Under Conditions of Normal Irrigation and Limited Irrigation Washed corn seeds of the FAO700 variety were inoculated by immersion for 16 h in a spore suspension at $10^6$ spores/ml, they were sown in substrate (peat and vermiculite at 3:1 ratio) and were kept in a controlled growth chamber at 23° C. When plants were 3 weeks old, they were taken to the field are where they were transplanted into the soil in four rows separated 70 cm and with a distance of 25 cm from plant to plant within each row. Control plants and plants inoculated with *C. tofieldiae* were planted in blocks randomly within each row. After a month with normal irrigation (100%), two of the rows were provided with limited irrigation with 30% of the irrigation with respect to the control plants. At the end of the growing cycle the number of grains per cob and each cob weight were recorded. The results are shown in Table 10. Plants treated with *C. tofieldiae* featured a 47% increase in grains and average weight per cob up to 70% when plants underwent limited irrigation.

Example 12: *Colletotrichum tofieldiae*, when Colonizing Plants, Produces an Increased Number of Grains Per Cob and Increased Weight of the Cobs Per Corn Plant Treated with the Isolate CECT 20833

Washed corn seeds of the FAO700 variety were sown into the soil in four rows separated 70 cm and with a distance of 25 cm from plant to plant within each row. For inoculation of *C. tofieldiae* a 200 ml/seed of peat vermiculite mixture were deposited onto the bottom of the seed furrow, at a concentration of $10^6$ UFC/ml which had been inoculated two weeks before with spores at a concentration of $10^6$ spores/ml of the isolate CECT 20833. Control plants and plants inoculated with *C. tofieldiae* were planted in blocks randomly within each row. At the end of the cultivation cycle, the number of grains per cob was counted. At the same time, a real time PCR (RT PCR) was performed for the anchoring roots tissue of the corn plants with primers CT RTPCR_L (SEQ ID NO: 1) and CT RTPCR_R (SEQ ID NO: 2), specific for *C. tofieldiae*. The results are shown in Table 11. The plants colonized with *C. tofieldiae* feature a production increase in cobs of up to 43% and an increase in the production of seeds of up to 35% when plant undergo limited irrigation with 30% of irrigation with respect to control plants.

TABLE 10

Average production of the number of grains (mean ± standard error) and weight per cob (mean ± standard error) of plants germinated from seeds treated with a spore suspension from *C. tofieldiae* under conditions of normal irrigation and limited irrigation.

| Treatment | N | Number of grains per cob | P-value | Average weight per cob | P-value |
|---|---|---|---|---|---|
| Normal irrigation (100%) | | | | | |
| Control | 19 | 439 ± 51 | — | 169 ± 19 | — |
| *C. tofieldiae* inoculation | 28 | 450 ± 36 (2%)* | 0.866 | 211 ± 17 (25%) | 0.119 |
| Limited irrigation (30%) | | | | | |
| Control | 17 | 267 ± 27 | — | 102 ± 24 | — |
| *C. tofieldiae* inoculation | 20 | 393 ± 56 (47%) | 0.063 | 173 ± 22 (70%) | 0.034* |

*Percentage increase compared between treated plants and untreated plants is indicated between brackets.
Different letters indicate significant differences in an ANOVA (P < 0.05).

TABLE 11

Average production (weight of cob per plant (mean ± standard error) and number of grains per plant (mean ± standard error), of plants germinated from seeds treated with a spore suspension from C. tofieldiae under normal irrigation conditions.

| Group | N | Average weight per cob | P-value | Average number of grains per plant | P-value |
|---|---|---|---|---|---|
| Control | 26 | 237 ± 19 | — | 574 ± 122 | — |
| *C. tofieldiae* | 7 | 339 ± 76 (42%) | 0.063 | 775 ± 48 (35%) | 0.079 |

The percentage increase compared between colonized and non-colonized plants is indicated between brackets. Different letters indicate significant differences in an ANOVA ($P < 0.05$).

ionic surfactants, cationic surfactants, water soluble polymers, polysaccharides, preservatives, coloring agents and/or stabilizing agents.

7. The method according to claim 6, wherein said minerals are selected from the group consisting of clay, bentonite, calcite, and diatomaceous cob, the organic materials are selected from the group consisting of corn powder or nut skin powder, said organic compound is urea, said inorganic compounds are selected from the group consisting of calcium carbonate, ammonium sulfate, silicon oxide, magnesium aluminum silicate, said liquid diluents are selected from the group consisting of aromatic hydrocarbons, aliphatic hydrocarbons, alcohols, ketones, vegetable oils,

The invention claimed is:

1. A method for increasing the production of flowers, seeds and/or fruits in a plant and/or part thereof, comprising:

(a) culturing *Colletotrichum tofieldiae* to produce a composition comprising spores, mycelia, hyphae, sclerotia, and/or filtrate of *C. tofieldiae*; and (b) contacting a plant and/or a part thereof, or a substrate for the cultivation of a plant with an effective amount of the composition, thereby increasing the production of flowers, seeds and/or fruits in the plant and/or part thereof, and/or in a plant and/or part thereof grown in the substrate.

2. The method according to claim 1, wherein said microorganism is a strain of *Colletotrichum tofieldiae* deposited under deposit numbers CECT 20833, CECT 20834, CECT 20835 or CECT 20836.

3. The method according claim 1, wherein the culturing of *C. tofieldiae* is in a solid or a liquid culture medium.

4. The method according to claim 1, wherein said composition is applied to aerial parts of the plant.

5. The method according to claim 1, wherein said composition is applied to the roots or other underground parts of the plant.

6. The method according to claim 1, wherein said composition comprises minerals, organic materials, organic compounds, inorganic compounds, liquid diluents, alcohols, ketones, vegetable oils, aliphatic hydrocarbons, esters, dimethyl sulfoxide, acetonitrile, water, anionic surfactants, nonesters, dimethyl sulfoxide, acetonitrile and water, said anionic surfactants are selected from the group consisting of salts of sulfate alkyl esters, alkylaryl sulfonate salts, dialkyl sulfosuccinate salts, salts of polyoxyethylene alkylaryl ether phosphate esters, polyoxyethylene lignosulfonate salts and formaldehyde polycondensates, said nonionic surfactants are selected from the group consisting of alkylaryl polyoxyethylene ethers, alkylpolyoxipropylene block copolymers, polyoxyethylene fatty acid esters, said cationic surfactants are alkyl trimethylammonium salts, said polymers are water soluble polyvinyl alcohol or polyvinylpyrrolidone, said polysaccharides are selected from the group consisting of agar, acacia, alginic acid, salts of alginic acid, carboxy methyl cellulose and xanthan gum and said stabilizing agents are isopropyl phosphate acid or BHT.

8. The method according to claim 7, wherein said aromatic hydrocarbons are selected from the group consisting of xylene, alkyl benzene, methyl naphthalene, said alcohols are selected from the group consisting of 2-propanol, ethylene glycol, propylene glycol and ethylene glycol monoethyl ether, said ketones are selected from the group comprising acetone, cyclohexanone and isophorone, and said vegetable oils are soybean oil or cottonseed oil.

9. The method according to claim 1, wherein said composition comprises substrate fertirrigation salts, fertilizers, insecticides, nematicides, fungicides, bactericides and/or herbicides.

10. The method according to claim 1, wherein said composition is a liquid, a solid, a paste or a gel.

11. The method according to claim 1, wherein said composition is a powder, pill, tablet, granule or an emulsifiable concentrate.

12. The method according to claim 1, wherein said composition is applied by spray, pulverization, immersion, irrigation or dusting.

13. The method according to claim 1, wherein said plant is a gymnosperms or dicot.

14. The method according to claim 1, wherein said plant is from the family Brassicaceae.

15. The method according to claim 1, wherein said plant is a monocot.

16. The method according to claim 1, wherein said plant is barley, rice, corn, wheat, soya, rape, tomato, bean, orange tree, lemon tree, or petunia.

17. The method according to claim 1, wherein the plant and/or part thereof is plant propagating material.

18. The method according to claim 17, wherein the plant propagating material comprises seeds, seedlings, plants, cuttings, cell suspensions, callus culture, tissue culture, protocorms, explants, germplasm, bulbs or tubers, or any combination thereof.

19. The method according to claim 3, wherein the solid or the liquid culture medium comprises dextrose, agar, plant parts, peat, vermiculite, paper, oat flour, potato, carrot, cellulose, cardboard, or polymers, or any combination thereof.

20. The method according to claim 19, wherein the plant parts comprise leaves, seeds, or pollen grains, or any combination thereof.

21. The method according to claim 1, wherein the composition further comprises a preservative.

22. The method according to claim 21, wherein the preservative is glycerol.

23. A substrate for plant cultivation comprising an effective amount of the composition of claim 1, wherein the substrate is liquid or solid, and wherein the effective amount of the composition increases the production of flowers, seeds, and/or fruits in a plant cultivated in the substrate, and wherein the substrate is a natural or synthetic media.

24. The substrate according to claim 23, wherein the substrate is soil, sand, humus, peat, vermiculite or a mixture thereof.

* * * * *